(12) United States Patent
Tachikawa et al.

(10) Patent No.: US 6,326,506 B1
(45) Date of Patent: Dec. 4, 2001

(54) METHOD OF PREPARING AN ORGANOSILICON COMPOUND

(75) Inventors: Mamoru Tachikawa; Kasumi Takei, both of Kanagawa (JP)

(73) Assignee: Dow Corning Asia, Ltd., Tokyo (JP)

(*) Notice: Subject to any disclaimer, the term of this patent is extended or adjusted under 35 U.S.C. 154(b) by 0 days.

(21) Appl. No.: 09/877,742

(22) Filed: Jun. 11, 2001

(51) Int. Cl.[7] ........................................ C07F 7/08
(52) U.S. Cl. ............................ 556/479; 549/215
(58) Field of Search ................ 556/479; 549/215

(56) References Cited

U.S. PATENT DOCUMENTS

| | | | |
|---|---|---|---|
| 4,292,433 | 9/1981 | Koga et al. | 556/479 |
| 5,359,111 | 10/1994 | Kleyer et al. | 556/479 |
| 5,449,802 | 9/1995 | Bank et al. | 556/479 |
| 5,481,016 | 1/1996 | Bank et al. | 556/479 |
| 5,481,637 | 1/1996 | Whitehead | 385/125 |
| 5,563,287 | 10/1996 | Roy | 556/479 |
| 5,567,848 | 10/1996 | Roy | 512/479 |
| 5,663,400 * | 9/1997 | Reitmeier et al. | 556/479 |
| 5,756,795 * | 5/1998 | Bank et al. | 556/479 |
| 6,048,994 * | 11/2000 | Tachikawa et al. | 556/479 |
| 6,054,602 * | 4/2000 | Tachikawa | 556/479 |
| 6,169,196 * | 1/2001 | Geisberger et al. | 556/479 |

FOREIGN PATENT DOCUMENTS

| | | |
|---|---|---|
| 09-157276 | 6/1997 | (JP) . |
| 09-192494 | 7/1997 | (JP) . |
| 10-072474 | 3/1998 | (JP) . |
| 11-080167 | 1/1999 | (JP) . |

* cited by examiner

*Primary Examiner*—Paul F. Shaver
(74) *Attorney, Agent, or Firm*—Roger E. Gobrogge

(57) ABSTRACT

A method of preparing an organosilicon compound comprising effecting a hydrosilylation reaction between (a) unsaturated compounds with terminal unsaturated groups and (b) silane compounds described by formula $HSiR^0{}_mW_{3-m}$, where W is selected from the group consisting of $C_1$ to $C_6$ alkoxy groups, $C_6$ to $C_{10}$ aryloxy groups, and halogen atoms, $R^0$ is an organic group, and m is 0, 1, or 2 in the presence of (c) a platinum catalyst and (d) an auxiliary catalyst selected from the group consisting of (1) silyl esters of acids derived from oxo acids of sulfur; (2) amide compounds having N—Si bonds; (3) urea compounds; (4) silyl esters of carbamic acid; (5) phosphoric acid compounds; and (6) cyclic compounds selected from the group consisting of (i) hydroxypyridine compounds, (ii) 8-hydroxyquinoline compounds, (iii) oxazolidinone compounds, and (iv) N-hydroxysuccinimide compounds.

14 Claims, No Drawings

METHOD OF PREPARING AN ORGANOSILICON COMPOUND

FIELD OF THE INVENTION

The present invention relates to the selective production of specific organosilicon compounds which are useful as silane coupling agents, as starting materials for various silicon compounds, are useful as various additives, and as starting materials for various organosilicon polymers.

BACKGROUND OF THE INVENTION

Hydrosilylation involving the use of platinum catalysts is a particularly important technique in the silicone industry, particularly in the production of organic modified silicones and silane coupling agents. Many attempts have been made in the past to improve the selectivity for the product structure or the hydrosilylation reaction rate in this process.

The following are examples of improvements in hydrosilylation reaction rates.

U.S. Pat. No. 5,359,111 describes a process where the hydrosilylation reaction is carried out in an oxygen gas atmosphere.

U.S. Pat. No. 5,449,802 describes a process where the hydrosilylation reaction is carried out in the presence of acetylene alcohol or a derivative thereof.

U.S. Pat. No. 5,481,016 describes a process where the hydrosilylation reaction is carried out in the presence of an alcohol having a tertiary structure or a derivative thereof.

U.S. Pat. No. 5,486,637 describes a process where the hydrosilylation reaction is carried out in the presence of alcohol having an unsaturated structure and a branched structure (tertiary or secondary) or a derivative thereof.

*Chem. Eur. J.* 1998, 4. No. 10, p. 2008–2017 describes a process where the hydrosilylation reaction is carried out in the presence of a naphthyl ketone.

Japanese Unexamined Patent Application (Kokai) 11-80167 describes a process where the hydrosilylation reaction is carried out in the presence of a sulfur compound.

Methods for bringing about a hydrosilylation reaction in the presence of a platinum catalyst and various additives have been proposed in order to improve the selectivity for certain products during hydrosilylation. The following are examples of reactions for the hydrosilylation of allyl chlorides with hydrochlorosilanes in the presence of a platinum catalyst. Japanese Unexamined Patent Application (Kokai) 9-157276 and Japanese Unexamined Patent Application (Kokai) 55-145693: phosphines are used as additives. Japanese Unexamined Patent Application (Kokai) 9-192494: tertiary amines with alkyl or aralkyl groups as substituents are used as additives. Japanese Unexamined Patent Application (Kokai) 10-72474: amino alcohol derivatives are used as additives.

U.S. Pat. No. 5,563,287 and U.S. Pat. No. 5,567,848 disclose methods featuring the use of cycloalkadiene compounds in the hydrosilylation of alkyne-based hydrocarbons.

Although the prior art discloses methods for improving the yield of the target product in specific systems, no method widely applicable to hydrosilylation reactions has yet been established for satisfactorily increasing the proportion of the target product over the proportion of by-products.

An object of the present invention is to allow target products (β-hydrosilylated products) having a structure in which silicon atoms are bonded to the terminal carbon atoms of unsaturated groups, which are the reactive groups of unsaturated compounds, to be produced more efficiently than in the past compared to by-products (substituted reaction products produced in the case of allyl chlorides and the like, or α-hydrosilylated products produced in the case of styrenes and the like) during hydrosilylation reactions in which the aforementioned unsaturated compounds having terminal unsaturated groups and silicon compounds having hydrogen atoms directly bonded to silicon atoms are allowed to react in the presence of a platinum catalyst.

SUMMARY OF THE INVENTION

A method of preparing an organosilicon compound comprising effecting a hydrosilylation reaction between (a) unsaturated compounds with terminal unsaturated groups and (b) silane compounds described by formula $HSiR^0{}_m W_{3-m}$, where W is a $C_1$ to $C_6$ alkoxy group, $C_6$ to $C_{10}$ aryloxy group, and halogen atoms, $R^0$ is an organic group, and m is 0, 1, or 2 in the presence of (c) a platinum catalyst and (d) an auxiliary catalyst selected from the group consisting of (1) silyl esters of acids derived from oxo acids of sulfur; (2) amide compounds having N—Si bonds; (3) urea compounds; (4) silyl esters of carbamic acid; (5) phosphoric acid compounds; and (6) cyclic compounds selected from the group consisting of (i) hydroxypyridine compounds, (ii) 8-hydroxyquinoline compounds, (iii) oxazolidinone compounds, and (iv) N-hydroxysuccinimide compounds.

DESCRIPTION OF THE INVENTION

The present invention is a method of preparing an organosilicon compound comprising effecting a hydrosilylation reaction between (a) unsaturated compounds with terminal unsaturated groups and (b) silane compounds described by formula $HSiR^0{}_m W_{3-m}$, where W is a $C_1$ to $C_6$ alkoxy group, $C_6$ to $C_{10}$ aryloxy group, and halogen atoms, $R^0$ is an organic group, and m is 0, 1, or 2 in the presence of (c) a platinum catalyst and (d) an auxiliary catalyst selected from the group consisting of (1) silyl esters of acids derived from oxo acids of sulfur; (2) amide compounds having N—Si bonds; (3) urea compounds; (4) silyl esters of carbamic acid; (5) phosphoric acid compounds; and (6) cyclic compounds described by the following formulas selected from the group consisting of (i) hydroxypyridine compounds, (ii) 8-hydroxyquinoline compounds, (iii) oxazolidinone compounds, and (iv) N-hydroxysuccinimide compounds:

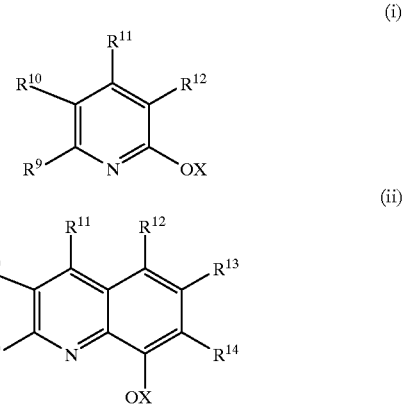

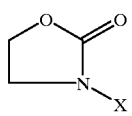

(iii)

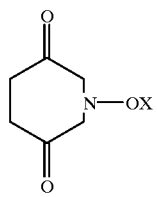

(iv)

where $R^9$, $R^{10}$, $R^{11}$, $R^{12}$, $R^{13}$, and $R^{14}$ are each independently selected from the group consisting of hydrogen atoms, halogen atoms, $C_1$ to $C_{10}$ alkyl groups, $C_6$ to $C_{10}$ aryl groups, $C_1$ to $C_{10}$ alkoxy groups, and groups described by $R^2{}_3Si—$, where each $R^2$ is independently selected from the group consisting of $C_1$ to $C_{10}$ hydrocarbon groups, $C_1$ to $C_{10}$ alkoxy groups, chlorine atoms, and hydrogen atoms with a maximum of 2 hydrogen atoms present; and X is a hydrogen atom or a group described by $R^2{}_3Si—$, where $R^2$ is the same as described above.

The aforementioned objectives are successfully achieved in the present invention by ensuring the presence of certain compounds during the aforementioned hydrosilylation reaction. The aforementioned certain compounds in the present invention are used as auxiliary catalysts during hydrosilylation reactions. Specifically, compounds are selected from among (d)(1) through (d)(6). Herein the compounds (d) are sometimes referred to as "substances acting as auxiliary catalysts" or "auxiliary catalyst". These auxiliary catalyst allow the target product to be produced preferentially over the aforementioned by-products in hydrosilylation reactions of (a) unsaturated compounds with terminal unsaturated groups in the range described below and (b) silane compounds represented by $HSiR^0{}_mW_{3-m}$, where each W is selected from the group consisting of $C_1$ to $C_6$ alkoxy groups, $C_6$ to $C_{10}$ aryloxy groups, and halogen atoms selected from F, Cl, Br, and I, $R^0$ is an organic group, and m is 0, 1, or 2, in the presence of (c) a platinum catalyst.

Depending on the type of system to which it is applied, the present method of hydrosilylation can also dramatically improve the yield of the target product and/or increase the reaction rate in addition to improving selectivity.

The components (a), (b), (c), and (d) used in the present method are described below.

The aforementioned (a) unsaturated compounds with terminal unsaturated groups refer to compounds having reactive carbon-carbon double bonds or carbon-carbon triple bonds at the terminals of the molecule. They are typically selected from among (1) through (8) below. These may include atoms selected from O, N, F, Cl, Br, Si, or S in addition to carbon atoms and hydrogen atoms in the structure, provided that the reactivity with the silane compound (b) above is not dramatically reduced. Component (a) can be, for example, (1) styrene or styrene derivatives;
(2) vinylsilane compounds;
(3) siloxane compounds having vinyl groups directly bonded to silicon atoms;
(4) epoxy functional olefins;
(5) diene compounds:
(6) allyl compounds represented by $CH_2=CHCH_2X$, where X is selected from the group consisting of a halogen atom i.e. F, Cl, Br, I, an alkoxy group, and acyloxy group;
(7) olefin compounds having terminal vinyl groups; and
(8) acetylene-based compounds.

Examples of (1) styrenes or styrene derivatives include styrene-based hydrocarbon compounds such as styrene, p-methylstyrene, p-ethylstyrene, p-phenylstyrene, and divinylbenzene; halogen-containing styrene such as p-fluorostyrene, p-chlorostyrene, p-bromostyrene, p-iodostyrene, and p- and m-(chloromethyl)styrene; oxygen-containing or silicon-containing styrene derivatives such as p-methoxystyrene and p-trimethylsilylstyrene; nitrogen-containing styrene derivatives such as p-(diphenylamino)styrene, p-(ditolylamino)styrene, p-(dixylylamino)styrene, and bis(4-vinylphenyl)(4-methylphenyl)amine.

Examples of (2) vinylsilane compounds and (3) siloxane compounds having vinyl groups directly bonded to silicon atoms include vinyltrialkylsilanes such as vinyltrimethylsilane, vinyltriethylsilane, vinyltripropylsilane, and vinyldimethylethylsilane; vinylalkoxysilanes such as vinyltrimethoxysilane, vinyltriethoxysilane, vinylmethyldiethoxysilane, and vinyldimethylmethoxysilane; vinyl functional siloxanes such as 1,3-divinyltetramethyldisiloxane, α, ω-divinylpolydimethylsiloxane, and 1,3,5,7-tetravinyl-1,3,5,7-tetramethylcyclotetrasiloxane; and vinyl functional silazanes (these can be viewed as a type of vinylsilane) such as 1,3-divinyltetramethyldisilazane and 1,3,5,7-tetravinyl-1,3,5,7-tetramethylcyclotetrasilazane.

Examples of (4) epoxy functional olefins include allyl glycidyl ethers and vinyl cyclohexene oxides. Examples of (5) diene compounds include 1,3-butadiene, isoprene, 1,5-hexadiene, and 1,3-octadiene. Examples of (6) allyl compounds described by $CH_2=CHCH_2X$ include allyl chlorides, allyl acetates, and allyl methacrylates.

Olefin compounds (7) having terminal vinyl groups may be straight-chained or branched. They may have aromatic hydrocarbon groups as substituents. Examples of straight-chained terminal unsaturated olefin compounds include ethylene, propylene, butene-1, hexene-1, octene-1, and octadecene-1. Examples of branched olefin compounds with terminal unsaturated groups include isobutylene, 3-methylbutene-1, 3,5-dimethylhexene-1, and 4-ethyloctene-1. Examples of olefin compounds which contain atoms selected from O, N, F, Cl, Br, Si, and S include oxygen-containing allyl compounds such as allyl methacrylates; amine compounds having vinyl groups such as N-vinylcarbazoles; olefin halogen compounds such as 4-chlorobutene-1 and 6-bromohexene-1; and silicon functional olefin compounds such as allyloxytrimethylsilane.

Acetylene-based compounds (8) have terminal ethynyl groups ($CH\equiv C—$). These may have aromatic hydrocarbon groups as substituents. Examples of acetylene-based compounds with terminal ethynyl groups ($CH\equiv C—$) include acetylene, propyne, butyne-1, hexyne-1, and octyne-1. Examples of acetylene-based compounds having aromatic hydrocarbon groups include phenylacetylene, 3-phenylpropyne, and 4-phenylbutyne-1. Examples of acetylene-based compounds which contain atoms selected from O, N, F, Cl, Br, Si, and S include oxygen-containing acetylene-based compounds such as 3-methyl-1-butyn-3-ol and 3-phenyl-1-butyn-3-ol; silicon-containing acetylene-based compounds such as O-trimethylsilyl compounds of 3-methyl-1-butyn-3-ol (HC≡C—CH(CH$_3$)—O—Si(CH$_3$)$_3$); and O-trimethylsilyl compounds of 3-phenyl-1-butyn-3-ol (HC≡C—CH(C$_6$H$_5$)—O—Si(CH$_3$)$_3$); and halogen-containing acetylene-based compounds such as propalgyl chloride and propalgyl bromide.

Silane compounds (b) described by HSiR$^0{}_m$W$_{3-m}$, where W is selected from the group consisting of C$_1$ to C$_6$ alkoxy groups, C$_6$ to C$_{10}$ aryloxy groups, and halogen atoms selected from F, Cl, Br, and I, R$^0$ is an organic group, and m is 0, 1, or 2 are described below.

Examples of R$^0$ include alkyl, alkenyl, aryl, haloalkyl, and haloaryl groups. Specific examples of R$^0$ include:

(1) C$_1$ to C$_{18}$ alkyls such as methyl, ethyl, n-propyl, isopropyl, n-butyl, t-butyl, n-pentyl, cyclohexyl, n-octyl, undecyl, and heptadecyl groups;

(2) C$_2$ to C$_{18}$ alkenyl groups such as propenyl groups and butenyl groups;

(3) C$_6$ to C$_{18}$ aryl groups such as phenyl;

(4) C$_1$ to C$_{18}$ haloalkyl groups (the halogen atom may be F, Cl, or Br) such as chloromethyl, fluoromethyl, and 3,3,3-trifluoropropyl groups; and (5) C$_6$ to C$_{18}$ haloaryl groups (the halogen atom may be F, Cl, or Br) such as p-chlorophenyl.

Examples where W is a C$_1$ to C$_6$ alkoxy group include methoxy, ethoxy, n-propoxy, i-propoxy, n-butoxy, n-pentyloxy, n-hexyloxy, cyclopentyloxy, cyclohexyloxy, 2-methoxyethoxy, and 2-ethoxyethoxy groups. Examples where W is a C$_6$ to C$_{10}$ aryloxy group include phenoxy. Examples where W is a halogen atom include those in which the halogen is selected from F, Cl, Br, or I, and preferably Cl or F.

A carbon number beyond the range stipulated here will result in reactivity that is too low for practical purposes for component (b). The following are preferred among the silane compounds of (b) for their reactivity: trimethoxysilane, methyldimethoxysilane, dimethylmethoxysilane, triethoxysilane, methyldiethoxysilane, dimethylethoxysilane, dimethylchlorosilane, methyldichlorosilane, and trichlorosilane.

The auxiliary catalyst in the present invention is a compound (d) which is copresent with the aforementioned (c) platinum catalyst during the hydrosilylation reaction so as to allow the target product (β-hydrosilylated products) having a structure in which silicon atoms are bonded to the terminal carbon atoms of unsaturated groups, which are the reactive groups of (a) unsaturated compounds having unsaturated terminal groups, to be produced more efficiently compared to the by-products.

The substance acting as an auxiliary catalyst comprising component (d) is selected from (1) through (6) below: (1) silyl esters of acids derived from oxo acids of sulfur; (2) amide compounds having N—Si bonds; (3) urea compounds; (4) silyl esters of carbamic acid; (5) phosphoric acid compounds; and (6) cyclic compounds represented by the following formulas, selected from (i) hydroxypyridine compounds, (ii) 8-hydroxyquinoline compounds, (iii) oxazolidinone compounds, and (iv) N-hydroxysuccinimide compounds:

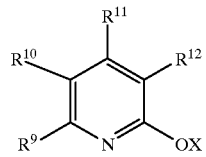
(i)

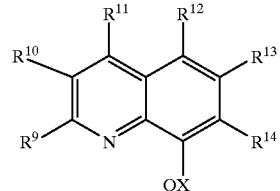
(ii)

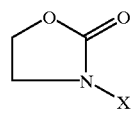
(iii)

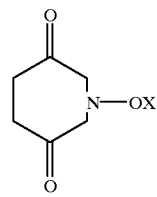
(iv)

where R$^9$, R$^{10}$, R$^{11}$, R$^{12}$, R$^{13}$, and R$^{14}$ are each independently selected from the group consisting of hydrogen atoms, halogen atoms selected from F, Cl, Br, and I, C$_1$ to C$_{10}$ alkyl groups, C$_6$ to C$_{10}$ aryl groups, C$_1$ to C$_{10}$ alkoxy groups, and groups described by R$^2{}_3$Si—, where each R$^2$ is independently selected from the group consisting of C$_1$ to C$_{10}$ hydrocarbon groups, C$_1$ to C$_{10}$ alkoxy groups, chlorine atoms, and hydrogen atoms with a maximum of 2 hydrogen atoms present; and X is hydrogen or a group described by R$^2{}_3$Si—, where R$^2$ is the same as described above.

Silyl esters of acids derived from oxo acids of sulfur in (d)(1) refer to silyl esters of acids derived from oxo acids of sulfur such as sulfonic acid and sulfuric acid, for example, alkylsulfonic acids, haloalkylsulfonic acids, arylsulfonic acids, haloarylsulfonic acids, halosulfuric acids, sulfamic acid, sulfuric acid monoesters, and sulfonic acids with siloxy groups directly bonded to sulfur atoms, and are not particularly limited, provided that these conditions are met. Preferably (d)(1) is compounds described by formula: R$^1$S(=O)$_2$ OSiR$^{21}{}_3$, where R$^1$ is selected from the group consisting of C$_1$ to C$_{10}$ alkyl groups, C$_6$ to C$_{18}$ aryl groups, groups described by R$^{18}{}_2$N—, where each R$^{18}$ is independently selected from the group consisting of C$_1$ to C$_{10}$ alkyl groups, C$_6$ to C$_{18}$ aryl groups, and hydrogen atoms with a maximum of 1 hydrogen atom present, C$_1$ to C$_{10}$ haloalkyl groups where the halogen atom is selected from F, Cl, Br, or I; (henceforth, halogen atoms are selected from F, Cl, Br, and I where "haloalkyls" are referred to), C$_6$ to C$_{18}$ haloaryl groups (halogen atoms are selected from F, Cl, Br, and I; henceforth, halogen atoms are selected from F, Cl, Br, or I where "haloaryls" are referred to), halogen atoms (selected from F, Cl, Br, and I), C$_1$ to C$_{10}$ alkoxy groups, and siloxy groups described by R$^{30}{}_3$SiO—, where each R$^{30}$ is an independently selected C$_1$ to C$_6$ alkyl groups; and each R$^{21}$ is independently selected from the group consisting of C$_1$ to C$_{10}$ hydrocarbon groups, C$_1$ to C$_{10}$ alkoxy groups, chlorine atoms, hydrogen atoms with a maximum of 2 hydrogen atoms present, and $R^1S(=O)_2O$—, where $R^1$ is the same as described above.

Examples of Silyl esters of acids derived from oxo acids of sulfur in (d)(1) include silyl esters of alkylsulfonic acids such as trimethylsilyl esters of methanesulfonic acid, silyl esters of arylsulfonic acids such as trimethylsilyl esters of benzenesulfonic acid, silyl esters of halosulfuric acid such as trimethylsilyl esters of chlorosulfuric acid (($CH_2)_3$ $SiOSO_2Cl$), diemethylsilyl esters of chlorosulfuric acid (($CH_3)_2HSiOSO_2Cl$), chloromethylsilyl esters of chlorosulfuric acid ($Cl(CH_3)HSiOSO_2Cl$), trimethylsilyl esters of chlorosulfuric acid (($CH_3)_3SiOSO_2F$), dimethylsilyl esters of fluorosulfuric acid (($CH_3)_2HSiOSO_2F$), and fluoromethylsilyl esters of fluorosulfuric acid ($F(CH_3)HSiOSO_2F$). Preferred examples are silyl esters of alkylsulfonic acids and silyl esters of arylsulfonic acids.

The amide compounds with N—Si bonds in (d)(2) have the amide group —$C(=O)$—$NR^{26}R^{27}$, where at least one of $R^{26}$ and $R^{27}$ consists of a silyl group and substituents that are not silyl groups are not particularly limited; examples include hydrogen atoms or hydrocarbon groups and are not particularly limited provided that these conditions are met. Component (d)(2) is preferably compounds described by formula: $R^3C(=O)NR^4SiR^{22}_3$, where $R^3$ is selected from the group consisting of $C_1$ to $C_{10}$ alkyl groups, $C_6$ to $C_{18}$ aryl groups, $C_1$ to $C_{10}$ haloalkyl groups, and $C_6$ to $C_{18}$ haloaryl groups; $R^4$ is a $C_1$ to $C_{10}$ hydrocarbon group or hydrogen atom; and each $R^{22}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^3C(=O)$ $NR^4$—, where $R^3$ and $R^4$ are the same as described above.

Examples of component (d)(2) include N-trimethylsilylformamide ($HC(=O)N(H)SiMe_3$)(Me is a methyl group, same below), N-dimethylsilylacetamide ($CH_3C(=O)N(H)SiMe_2H$), N-trimethylsilylpropionamide ($CH_3CH_2C(=O)N(H)SiMe_3$), N-dimethylsilylbenzamide ($PhC(=O)N(H)SiMe_2H$)(Ph is a phenyl group, same below), N-trimethylsilyltrifluoroacetamide ($CF_3C(=O)N$ $(H)SiMe_3$), N-trimethylsilyl-N-methyl formamide (HC $(=O)N(Me)SiMe_3$), N-dimethylsilyl-N-methylacetamide ($CH_3C(=O)N(Me)SiMe_2H$), N-trimethylsilyl-N-ethylpropionamide ($CH_3CH_2C(=O)N(Et)SiMe_3$)(Et is an ethyl group, same below), N-trimethylsilyl-N-methylbenzamide ($PhC(=O)N(Me)SiMe_3$), N-dimethylsilyl-N-ethyltrifluoroacetamide ($CF_3C(=O)N$ $(Et)SiMe_2H$), N,N-bis(trimethylsilyl)formamide ($HC(=O)$ $N(SiMe_3)_2$), and N,N-bis(dimethylsilyl)acetamide ($CH_3C$ $(=O)N(SiMe_2H)_2$). N-dialkylsilylacetamides and N-dialkylsilyl-N-alkylacetamides are preferred.

The urea compounds in (d)(3) have a >N—C(=O)—N< structure, and are not particularly limited provided that this condition is met. The urea compounds are preferably compounds described by formula: $R^5R^6NC(=O)NR^4X^1$, where $R^5$ and $R^6$ are each independently selected from the group consisting of hydrogen atoms, $C_1$ to $C_{10}$ alkyl groups, $C_6$ to $C_{18}$ aryl groups, $C_1$ to $C_{10}$ haloalkyl groups, $C_6$ to $C_{18}$ haloaryl groups, and silyl groups represented by $R_3Si$—, where each R is an independently selected $C_1$ to $C_3$ alkyl group or hydrogen atom with a maximum of 2 hydrogen atoms present, $R^4$ is the same as described above; $X^1$ is selected from the group consisting of $R^{23}_3Si$—$^6$ and hydrogen atoms; where each $R^{23}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^5R^6NC$ $(=O)$—, where $R^5$ and R—$^6$ are as described above.

Examples of compounds of component (d)(3) include urea, N-methylurea ($H_2NC(=O)N(H)CH_3$), N,N-dimethylurea ($H_2NC(=O)N(CH_3)_2$)), N-trimethylsilylurea ($H_2NC(=O)N(H)SiMe_3$), N,N'-bis(trimethylsilyl)urea ($Me_3Si(H)NC(=O)N(H)SiMe_3$), N,N'-dimethyl-N,N'-bis (trimethylsilyl)urea ($Me_3Si(CH_3)NC(=O)N(CH_3)SiMe_3$), and N,N'-bis(dimethylsilyl)urea ($Me_2HSi(H)NC(=O)N(H)$ $SiMe_3H$). Urea or N,N'-bis(trialkylsilyl)ureas are preferred.

The silyl esters of carbamic acids in (d)(4) are silyl esters of well-known carbamic acids (those with an >NC(=O)OH structure), and are not particularly limited, provided that this condition is met. The silyl esters of carbamic acids are preferably compounds described by formula: $R^7R^8NC(=O)$ $OSiR^{24}_3$, where $R^7$ and $R^8$ are each independently selected from the group consisting of $C_1$ to $C_{10}$ alkyl groups, $C_6$ to $C_{18}$ aryl groups, and hydrogen atoms with a maximum of 1 hydrogen atom present; and each $R^{24}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^7R^8NC(=O)$—, where $R^7$ and $R^8$ are the same as above.

Examples of compounds of component (d)(4) include dimethylsilyl N-methylcarbamate ($CH_2(H)C(=O)$ $OSiMe_2H$), trimethylsilyl N-ethylcarbamate ($Et(H)C(=O)$ $OSiMe_3$), dimethylsilyl N-phenylcarbamate ($Ph(H)C(=O)$ $OSiMe_3H$), dimethylsilyl N,N-dimethylcarbamate (($CH_3)_2C$ $(=O)OSiMe_2H$), and trimethylsilyl N,N-diethylcarbamate ($Et_2C(=O)OSiMe_3$). Trialkylsilyl N,N-dialkylcarbamates are preferred.

The phosphoric acid compounds of (d)(5) are not particularly limited, provided that they are compounds derived from ortho-phosphoric acid. Phosphoric acid compounds are preferably compounds described by formula: $(R^{16}O)_3P$ $(=O)$, where each $R^{16}$ is independently selected from the group consisting of hydrogen atoms with a maximum of 2 hydrogen atoms present, $C_1$ to $C_{10}$ alkyl groups, $C_6$ to $C_{18}$ aryl groups, $C_1$ to $C_{10}$ haloalkyl groups, $C_6$ to $C_{18}$ haloaryl groups, and silyl groups described by $R^{25}_3Si$—, where each $R^{25}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present), and $(R^{15}O)_2P(=O)O$—, where each $R^{15}$ is independently selected from the group consisting of hydrogen atoms with a maximum of 2 hydrogen atoms present, $C_1$ to $C_{10}$ alkyl groups, $C_6$ to $C_{18}$ aryl groups, $C_1$ to $C_{10}$ haloalkyl groups, and $C_6$ to $C_{18}$ haloaryl groups with a maximum of 2 silyl groups present.

Examples of compounds of component (d)(5) include triethyl phosphate (($EtO)_3P(=O)$), trimethyl phosphate (($MeO)_3P(=O)$), tris(butoxyethyl) phosphate (($BuOCH_2CH_2O)_3P(=O)$)(Bu is a butyl group, same below), bis(2-ethylhexyl) hydrogen phosphate ($C_4H_9CH$ $(C_2H_5)CH_2O)_2P(=O)OH$), and tris(4-t-butylphenyl) phosphate ($(4-tBu-Ph-O)_3PO$). Trialkyl phosphates are preferred.

Examples of cyclic compounds selected from the (i) hydroxypyridine compounds, (ii) 8-hydroxyquinoline compounds, (iii) oxazolidinone compounds, and (iv) N-hydroxysuccinimide compounds of (d)(6) include 2-hydroxypyridine, 8-hydroxyquinoline, oxazolidinone, and 3-trimethylsilyl-2-oxazolidinone, and N-hydroxysuccinimide. The hydrogen atom of the hydroxy groups in such compounds may be substituted with silyl groups such as trimethylsilyl, dimethylsilyl, methylsilyl, trimethoxysilyl, dimethoxysilyl, methylchlorosilyl, and dichlorosilyl groups.

In the present invention, a substance acting as an auxiliary catalyst selected from (d)(1) through (6) above is present in the hydrosilylation reaction mixture. The copresence of this substance acting as an auxiliary catalyst with the reaction substrate (components (a) and (b)) and the platinum catalyst of component (c) usually promotes the hydrosilylation reaction.

However, a substance producing the substance that acts as the auxiliary catalyst through a chemical reaction (henceforth referred to as "substance producing a substance that acts as an auxiliary catalyst" or "in situ produced auxiliary catalyst") can be used in the hydrosilylation reaction mixture as an alternative to the aforementioned substance acting as an auxiliary catalyst.

Specific examples include methods in which a substance producing a substance that acts as an auxiliary catalyst is present with the reaction substrate and platinum catalyst so that the substance acting as an auxiliary catalyst is produced by a chemical reaction in the system from the substance producing the substance that acts as an auxiliary catalyst, thereby promoting the hydrosilylation reaction, and methods in which a substance producing a substance that acts as an auxiliary catalyst is allowed to be present with part or all of the reaction substrate to similarly produce a substance acting as an auxiliary catalyst, and other components needed for the hydrosilylation reaction are subsequently added to promote the reaction. The present invention includes such methods.

The aforementioned substance producing a substance that acts as an auxiliary catalyst is not particularly limited, provided that it produces a substance acting as an auxiliary catalyst selected from (d)(1) through (d)(6) above.

Typical examples of substances producing a substance that acts as an auxiliary catalyst include metal salt compounds that produce the substances acting as auxiliary catalysts selected from (d)(1) through (d)(6) in the hydrosilylation reaction mixture. Such metal salt compounds produce substances acting as auxiliary catalysts upon reaction with chlorosilanes, particularly when component (b) is a chlorosilane represented by $R_{3-n}Cl_nSiH$, where R is a $C_1$ to $C_3$ alkyl group, and n is an integer of 1 to 3. Examples of such metal salt compounds include metal salts of acids derived from oxo acids of sulfur, metal salts of amide compounds having NH groups, metal salts of carbamic acids, and metal salts of phosphoric acid compounds having OH groups. Alkali metals or alkaline earth metals can be used, for examples, as the metals of such metal salts. Examples include Na, K, and Li.

Specific examples of metal salts of acids derived from oxo acids of sulfur include sodium methanesulfonate, sodium 1-octanesulfonate $(C_8H_{17}—S(=O)_2ONa)$, sodium cyclohexylsulfamate $(C_5H_9—NH—S(=O)_2ONa)$, sodium dodecylsulfate $(CH_3(CH_2)_{10}CH_2OSO_3Na)$, and sodium benzenesulfonate. These produce silyl esters of acids derived from oxo acids of sulfur upon reaction with the aforementioned chlorosilanes. Dimethyl chlorosilane $((CH_3)_2ClSiH)$ is an example of such a chlorosilane.

Other examples of metal salts include potassium salts of N-methylacetamide $(CH_3C(=O)N(CH_3)K)$ and monolithium salts of diethylphosphate esters $((C_2H_5O)_2P(=O)OLi)$. Amide compounds with N—Si bonds and phosphate compounds are similarly produced upon reaction with chlorosilanes.

The substance acting as an auxiliary catalyst (component (d)) can be used within the range of between 0.01 and 20 wt % relative to the total amount of the reaction substrate (components (a) and (b)). An amount lower than this range will generally result in lower effects, while an amount greater than this range can cause problems in terms of the cost of the substance acting as the auxiliary catalyst, difficulties in removing the substance acting as the auxiliary catalyst, side reactions, and so forth, and thus will not always necessarily provide desirable results. When the effects of the substance acting as the auxiliary catalyst improves reaction selectivity at the expense of the reaction rate, the amount that is added must be limited in order to avoid unduly lowering the reaction rate. The amount added should generally range from 0.05 to 10 wt % to ensure satisfactory results and for economic reasons.

The ratio in which the reaction substrate components (a) and (b) are blended is not particularly restricted, and is selected as befits the specific purpose, such as the yield or amount obtained when implementing the present invention.

The amount in which the reaction catalyst component (c) is used is not particularly limited, provided that the desired hardening properties are obtained. However, for economic reasons, the catalyst is generally used in the range of $10^{-8}$ mol to $10^{-3}$ mol platinum per mol silane compound component (b).

There is no essential need to use a solvent in the present invention, but hydrocarbon compounds can be used as reaction solvents or catalyst component solvents to dissolve the substrate as well as to facilitate the addition of the catalyst components and control the temperature of the reaction system. Examples of solvents which are ideal for such purposes include saturated or unsaturated hydrocarbon compounds such as hexane, cyclohexane, heptane, octane, dodecane, benzene, toluene, xylene, and dodecylbenzene; and halohydrocarbon compounds such as chloroform, methylene chloride, chlorobenzene, and ortho-dichlorobenzene.

Specific examples of (c) platinum catalysts which may be used as the hydrosilation catalyst in the present invention include, but are not limited to, olefin complexes of 0-valent platinum, vinylsiloxane complexes of 0-valent platinum, olefin complex-halogen compounds of divalent platinum, chloroplatinic acid, carbon-supported platinum, and silica-supported platinum, as well as others common industrially used types.

The hydrosilylation reaction in the present invention is preferably carried out at a temperature between 10 and 250° C.

The method for producing organosilicon compounds through the hydrosilylation of unsaturated compounds in the present invention is applicable to hydrosilylation reactions in which the reaction is brought about between a wide range of unsaturated compounds and silicon compounds with hydrogen atoms directly bonded to silicon atoms in the presence of a platinum catalyst. The advantage is that the product (β-hydrosilylated product or terminal hydrosilylated product) comprising hydrosilylated terminal carbon atoms (β position carbon atoms) in the unsaturated groups can be produced preferentially (selectively) over by-products.

As used herein, by-products mean materials comprising hydrosilylated α-position carbon atoms in unsaturated groups (α-hydrosilylated products) or materials that are produced by reactions (generally substitution reactions) other than hydrosilylation. In addition to the selectivity for products, the yield can be improved and the reaction rate can be dramatically increased, depending on the type of reaction system to which the present invention is applied.

EXAMPLES

Examples and comparative examples are given below to illustrate the invention in further detail, but the present invention is not limited to these examples alone.

Products in the following examples were analyzed through comparison with standard samples using gas chromatography and gas chromatographic mass analysis. The conversion rate indicates the reaction rate relative to the olefin starting material used, and the yield similarly indicates the proportion of product produced relative to the amount of olefin starting material used.

The N-dimethylsilyl-N-methylacetamide used in the examples was synthesized from dimethylchlorosilane and N-methylacetamide. Commercially available additives, hydridohalosilane compounds, and unsaturated compounds were otherwise used.

Example 1

Reaction between styrene and triethoxysilane with platinum catalyst in the presence of trimethylsilyl methanesulfonate. 356 mg Styrene and 562 mg triethoxysilane were introduced into a glass tube, and 25 mg of trimethylsilyl methanesulfonate $((CH_3)_3SiOSO_2CH_3)$ were added using a microsyringe. 0.005 ml (4.3 mg) of a toluene solution of a 0-valent platinum complex of divinyltetramethyldisiloxane (0.04 wt % platinum content) was added. The tube was sealed with Teflon tape and a rubber septum and placed in a 80° C. oil bath and heated for 2 hours. After cooling, the tube contents were analyzed by gas chromatography, revealing a styrene conversion of about 10% and a hydrosilylated product yield of 9.5%. The ratio between the terminal hydrosilylated product (phenethyl triethoxysilane) and the interior hydrosilylated product (α-(triethoxysilyl) ethylbenzene) was 53:1.

Example 2

Reaction between styrene and triethoxysilane with platinum catalyst in the presence of trimethylsilyl benzenesulfonate. 356 mg Styrene and 562 mg triethoxysilane were introduced into a glass tube, and 10 mg of trimethylsilyl benzenesulfonate $((CH_3)_3SiOSO_2C_6H_5)$ were added using a microsyringe. 0.005 ml (4.3 mg) of a toluene solution of a 0-valent platinum complex of divinyltetramethyldisiloxane (0.04 wt % platinum content) was added. The tube was sealed with Teflon tape and a rubber septum and placed in a 80° C. oil bath where it was heated for 2 hours. After cooling, the tube contents were analyzed by gas chromatography revealing a styrene conversion of about 8.5% and a hydrosilylated product yield of 8.4%. The ratio between the terminal hydrosilylated product (phenethyl triethoxysilane) and the interior hydrosilylated product (α-(triethoxysilyl) ethylbenzene) was 19.2:1.

Example 3

Reaction between styrene and triethoxysilane with platinum catalyst in the presence of 2-hydroxypyridine. 353 mg Styrene and 557 mg triethoxysilane were introduced into a glass tube, and 11.3 mg of 2-hydroxypyridine was added. 0.005 ml (4.3 mg) Of a toluene solution of a 0-valent platinum complex of divinyltetramethyldisiloxane (0.04 wt % platinum content) was added. The tube was sealed with Teflon tape and a rubber septum and placed in a 80° C. oil bath where it was heated for 2 hours. After cooling, the tube contents were analyzed by gas chromatography revealing a hydrosilylated product yield of 11.5%. The ratio between the terminal hydrosilylated product (phenethyl triethoxysilane) and the interior hydrosilylated product (α-(triethoxysilyl) ethylbenzene) was 15:1.

Example 4

Reaction between styrene and triethoxysilane with platinum catalyst in the presence of N-dimethylsilyl-N-methylacetamide. 473 mg Styrene and 721 mg triethoxysilane were introduced into a glass tube, and 10 mg of N-dimethylsilyl-N-methylacetamide were added using a microsyringe. 0.005 ml (4.3 mg) Of a toluene solution of a 0-valent platinum complex of divinyltetramethyldisiloxane (0.04 wt % platinum content) was added. The tube was sealed with Teflon tape and a rubber septum and placed in a 80° C. oil bath where it was heated for 1 hour. After cooling, the tube contents were analyzed by gas chromatography revealing a styrene conversion of about 68% and a hydrosilylated product yield of 63%. The ratio between the terminal hydrosilylated product (phenethyl triethoxysilane) and the interior hydrosilylated product (α-(triethoxysilyl) ethylbenzene) was 43:1.

Example 5

Reaction between styrene and triethoxysilane with platinum catalyst in the presence of bis(2-ethylhexyl) hydrogenphosphate $(C_4H_9CH(C_2H_5)CH_2O)_2P(=O)OH)$. 0.334 g Styrene and 0.540 g triethoxysilane were introduced into a glass tube, and 3 mg of bis(2-ethylhexyl) hydrogenphosphate were added using a microsyringe. 0.8 mg Of a toluene solution of a 0-valent platinum complex of divinylsiloxane (0.4 wt % platinum content) was added. The tube was sealed with Teflon tape and a septum and placed in a 100° C. oil bath where it was heated for 1 hour. After cooling, the tube contents were analyzed by gas chromatography revealing a styrene conversion of about 29% and a phenethyl triethoxysilane yield of 16%. The ratio between the phenethyl triethoxysilane and the (α-methylbenzyl)triethoxysilane was 5.8:1.

Comparative Example 1

Reaction between styrene and triethoxysilane with platinum catalyst (no substance acting as auxiliary catalyst). 356 mg Styrene and 562 mg triethoxysilane were introduced into a glass tube, and 0.005 ml (4.3 mg) of a toluene solution of a 0-valent platinum complex of divinyltetramethyldisiloxane (0.04 wt % platinum content) was added. The tube was sealed with Teflon tape and a rubber septum and placed in a 80° C. oil bath where it was heated for 2 hours. After cooling, the tube contents were analyzed by gas chromatography revealing a styrene conversion of about 0.5% and a hydrosilylated product yield of 0.3%. The ratio between the terminal hydrosilylated product (phenethyl triethoxysilane) and the interior hydrosilylated product (α-(triethoxysilyl) ethylbenzene) was 2.3:1.

Comparative Example 2

Reaction between styrene and triethoxysilane with platinum catalyst (no substance acting as auxiliary catalyst). 353 mg Styrene and 557 mg triethoxysilane were introduced into a glass tube, and 0.005 ml (4.3 mg) of a toluene solution of a 0-valent platinum complex of divinyltetramethyldisiloxane (0.04 wt % platinum content) was added. The tube was sealed with Teflon tape and a rubber septum and placed in a 80° C. oil bath where it was heated for 2 hours. After cooling, the tube contents were analyzed by gas chromatography revealing a hydrosilylated product yield of 11.3%. The ratio between the terminal hydrosilylated product (phenethyl triethoxysilane) and the interior hydrosilylated product (α-(triethoxysilyl)ethylbenzene) was 1.9:1.

Example 6

Reaction between octene-1 and triethoxysilane with platinum catalyst in the presence of trimethylsilyl ester of methanesulfonic acid. 325 mg Octene-1 and 475 mg triethoxysilane were introduced into a glass tube filled with argon gas, and 20 mg of a trimethylsilyl ester of methanesulfonic acid and 0.002 ml (1.7 mg) of a toluene solution of a 0-valent platinum complex of divinyltetramethyldisiloxane (0.04 wt % platinum content) were added. The tube was sealed with Teflon tape and a rubber septum, degassed, and then filled again with argon gas. The tube was placed in a 75° C. oil bath where it was heated for 1 hour. After cooling, the tube contents were analyzed by gas chromatography revealing an octyltriethoxysilane yield of 88%.

Comparative Example 3

Reaction between octene-1 and triethoxysilane with platinum catalyst (no substance acting as auxiliary catalyst). 325 mg Octene-1 and 475 mg triethoxysilane were introduced into a glass tube filled with argon gas, and 0.002 mL (1.7 mg) of a toluene solution of a 0-valent platinum complex of divinyltetramethyldisiloxane (0.04 wt % platinum content) were added. The tube was sealed with Teflon tape and a rubber septum, degassed, and then filled again with argon gas. The tube was placed in a 75° C. oil bath where it was heated for 1 hour. After cooling, the tube contents were analyzed by gas chromatography revealing that the starting material was unreacted, with no octyltriethoxysilane product.

Example 7

Reaction between allylglycidyl ether and triethoxysilane with platinum catalyst in the presence of N-dimethylsilyl-N-methylacetamide. 548 mg Allylglycidyl ether and 408 mg triethoxysilane were introduced into a glass tube filled with argon gas, and 10 mg of N-dimethylsilyl-N-methylacetamide and 0.005 mL (4.3 mg) of a toluene solution of a 0-valent platinum complex of divinyltetramethyldisiloxane (0.04 wt % platinum content) were added. The tube was sealed with Teflon tape and a rubber septum, degassed, and then filled again with argon gas. The tube was placed in a 100° C. oil bath where it was heated for 0.5 hour. After cooling, the tube contents were analyzed by gas chromatography revealing a triethoxysilane conversion of 39% and a glycidoxy propyltriethoxysilane yield of 87 mol % relative to consumed triethoxysilane. The ratio between the 3-(glycidoxy) propyltriethoxysilane and 2-(glycidoxy)-1-(methyl)ethyltriethoxysilane was 1960:1.

Comparative Example 4

Reaction between allylglycidyl ether and triethoxysilane with platinum catalyst (no substance acting as auxiliary catalyst). 548 mg Allylglycidyl ether and 408 mg triethoxysilane were introduced into a glass tube filled with argon gas, and 0.005 mL (4.3 mg) of a toluene solution of a 0-valent platinum complex of divinyltetramethyldisiloxane (0.04 wt % platinum content) were added. The tube was sealed with Teflon tape and a rubber septum, degassed, and filled again with argon gas. The tube was placed in a 100° C. oil bath where it was heated for 0.5 hour. After cooling, the tube contents were analyzed by gas chromatography revealing a triethoxysilane conversion of 98%, and a glycidoxy propyltriethoxysilane yield of 87 mol % relative to consumed triethoxysilane. The ratio between the 3-(glycidoxy)propyltriethoxysilane and 2-(glycidoxy)-1-(methyl) ethyltriethoxysilane was 90:1.

Example 8

Reaction between styrene and dimethylchlorosilane with platinum catalyst in the presence of trimethylsilyl-N,N-dimethyl carbamate. 526 mg Styrene and 480 mg dimethylchlorosilane were introduced into a glass tube, and 41 mg of trimethylsilyl-N,N-dimethyl carbamate were added using a microsyringe. 0.65 mg Of a toluene solution of a 0-valent platinum complex of divinylsiloxane (0.4 wt % platinum content) was added. The tube was sealed with Teflon tape and a rubber septum and placed in a 100° C. oil bath where it was heated for 20 hours. After cooling, the tube contents were analyzed by gas chromatography revealing a styrene conversion of 38% and a phenethyl dimethylchlorosilane yield of 8.4%. The ratio between the phenethyl dimethylchlorosilane and the (α-methylbenzene) dimethylchlorosilane was 44:1.

Example 9

Reaction between styrene and dimethylchlorosilane with platinum catalyst in the presence of N-dimethylsilyl-N-methylacetamide. 526 mg Styrene and 408 mg dimethylchlorosilane were introduced into a glass tube, and 1 mg of N-dimethylsilyl-N-methylacetamide was added. 2.5 mg Of a toluene solution of a 0-valent platinum complex of divinylsiloxane (0.04 wt % platinum content) were added. The tube was sealed with Teflon tape and a rubber septum and then placed in a 50° C. oil bath where it was heated for 30 minutes. After cooling, the tube contents were analyzed by gas chromatography revealing a styrene conversion of 4.8% and a phenethyldimethylchlorosilane yield of 4.4%. The ratio between the phenethyldimethylchlorosilane and (α-methylbenzyl)dimethylchlorosilane was 15:1.

Comparative Example 5

Reaction between styrene and dimethylchlorosilane with platinum catalyst (no substance acting as auxiliary catalyst). 526 mg Styrene and 408 mg dimethylchlorosilane were introduced into a glass tube, and 2.5 mg of a toluene solution of a 0-valent platinum complex of divinylsiloxane (0.04 wt % platinum content) were added. The tube was sealed with Teflon tape and a rubber septum and then placed in a 50° C. oil bath where it was heated for 30 minutes. After cooling, the tube contents were analyzed by gas chromatography revealing a styrene conversion of 98% and a phenethyldimethylchlorosilane yield of 84%. The ratio between the phenethyldimethylchlorosilane and (α-methylbenzyl) dimethylchlorosilane was 4.7:1.

Example 10

Reaction between styrene and methyldichlorosilane with platinum catalyst in the presence of trimethylsilyl ester of methanesulfonic acid. 624 mg Styrene and 732 mg methyldichlorosilane were introduced into a glass tube, and 51 mg of a trimethylsilyl ester of methanesulfonic acid was added with a microsyringe. 0.9 mg Of a toluene solution of a 0-valent platinum complex of divinylsiloxane (0.04 wt % platinum content) was added. The tube was sealed with Teflon tape and a rubber septum and placed in a 50° C. oil bath where it was heated for 30 minutes. After cooling, the tube contents were analyzed by gas chromatography revealing a styrene conversion of 95% and a phenethylmethyldichlorosilane yield of 71%. The ratio between the phenethylmethyldichlorosilane and the (α-methylbenzyl) methyldichlorosilane was 4.6:1.

Example 11

Reaction between styrene and methyldichlorosilane with platinum catalyst in the presence of trimethylsilyl ester of benzenesulfonic acid. 624 mg Styrene and 732 mg methyldichlorosilane were introduced into a glass tube, and 54 mg of a trimethylsilyl ester of benzenesulfonic acid were added with a microsyringe. 0.9 mg of a toluene solution of a 0-valent platinum complex of divinylsiloxane (0.04 wt % platinum content) was added. The tube was sealed with Teflon tape and a rubber septum and then placed in a 50° C. oil bath where it was heated for 30 minutes. After cooling, the tube contents were analyzed by gas chromatography revealing a styrene conversion of 27% and a phenethylmethyldichlorosilane yield of 19%. The ratio between the phenethylmethyldichlorosilane and the ($\alpha$-methylbenzyl)methyldichlorosilane was 4.2:1.

Example 12

Reaction between styrene and methyldichlorosilane with platinum catalyst in the presence of sodium 1-octanesulfonate. 624 mg Styrene and 732 mg methyldichlorosilane were introduced into a glass tube, and 40 mg of sodium 1-octanesulfonate were added with a microsyringe. 0.9 mg Of a toluene solution of a 0-valent platinum complex of divinylsiloxane (0.04 wt % platinum content) was added. The tube was sealed with Teflon tape and a rubber septum and then placed in a 100° C. oil bath where it was heated for 20 minutes. After cooling, the tube contents were analyzed by gas chromatography revealing a styrene conversion of 71% and a phenethylmethyldichlorosilane yield of 46%. The ratio between the phenethylmethyldichlorosilane and the ($\alpha$-methylbenzyl)methyldichlorosilane was 18:1.

Example 13

Reaction between styrene and methyldichlorosilane with platinum catalyst in the presence of N,N'-bis(trimethylsilyl)urea. 0.481 g Styrene and 0.549 g methyldichlorosilane were introduced into a glass tube, and an ethanol solution containing 0.124 mg N,N'-bis(trimethylsilyl)urea (6.2 wt %) was added with a microsyringe. 1 mg Of a toluene solution of a 0-valent platinum complex of divinylsiloxane (0.04 wt % platinum content) was added. The tube was sealed with Teflon tape and a septum and then placed in a 100° C. oil bath where it was heated for 20 minutes. After cooling, the tube contents were analyzed by gas chromatography revealing a styrene conversion of 89% and a phenethylmethyldichlorosilane yield of 84%. The ratio between the phenethylmethyldichlorosilane and the ($\alpha$-methylbenzyl)methyldichlorosilane was 21:1.

Example 14

Reaction between styrene and methyldichlorosilane with platinum catalyst in the presence of urea. 0.384 g Styrene and 0.435 g methyldichlorosilane were introduced into a glass tube, and an ethanol solution containing 0.255 mg urea (5.1 wt %) was added with a microsyringe. 1 mg Of a toluene solution of 0-valent platinum complex of divinylsiloxane (0.04 wt % platinum content) was added. The reaction tube was sealed with Teflon tape and a septum and placed in a 100° C. oil bath where it was heated for 20 minutes. After cooling, the tube contents were analyzed by gas chromatography revealing a styrene conversion of 64% and a phenethylmethyldichlorosilane yield of 61%. The ratio between the phenethylmethyldichlorosilane and the ($\alpha$-methylbenzyl)methyldichlorosilane was 102:1.

Comparative Example 6

Reaction between styrene and methyldichlorosilane with platinum catalyst (no substance acting as auxiliary catalyst). 624 mg Styrene and 732 mg methyldichlorosilane were introduced into a glass tube, and 0.9 mg of a toluene solution of a 0-valent platinum complex of divinylsiloxane (0.04 wt % platinum content) was added. The tube was sealed with Teflon tape and a rubber septum and placed in a 50° C. oil bath where it was heated for 30 minutes. After cooling, the tube contents were analyzed by gas chromatography revealing a styrene conversion of 75% and a phenethylmethyldichlorosilane yield of 22%. The ratio between the phenethylmethyldichlorosilane and the ($\alpha$-methylbenzyl)methyldichlorosilane was 1.2:1.

Example 15

Reaction between styrene and trichlorosilane with platinum catalyst in the presence of a trimethylsilyl ester of methanesulfonic acid. 518 mg Styrene and 694 mg trichlorosilane were introduced into a glass tube, and 42 mg of a trimethylsilyl ester of methanesulfonic acid were added. 2.5 mg Of a toluene solution of a 0-valent platinum complex of divinylsiloxane (0.04 wt % platinum content) were added. The tube was sealed with Teflon tape and a rubber septum and placed in a 50° C. oil bath where it was heated for 30 minutes. After cooling, the tube contents were analyzed by gas chromatography revealing a styrene conversion of 11% and a phenethyltrichlorosilane yield of 8.7%. The ratio between the phenethyltrichlorosilane and the ($\alpha$-methylbenzyl)trichlorosilane was 390:1.

Comparative Example 7

Reaction between styrene and trichlorosilane with platinum catalyst (no substance acting as auxiliary catalyst). 518 mg Styrene and 694 mg trichlorosilane were introduced into a glass tube, and 2.5 mg of a toluene solution of a 0-valent platinum complex of divinylsiloxane (0.04 wt % platinum content) were added. The tube was sealed with Teflon tape and a rubber septum and then placed in a 50° C. oil bath where it was heated for 30 minutes. After cooling, the tube contents were analyzed by gas chromatography revealing a styrene conversion of 93% and a phenethyltrichlorosilane yield of 39%. The ratio between the phenethyltrichlorosilane and the ($\alpha$-methylbenzyl)trichlorosilane was 5.5:1.

Example 16

Reaction between allyl chloride and methyldichlorosilane with platinum catalyst in the presence of N-dimethylsilyl-N-methylacetamide. 0.405 g Allyl chloride and 0.912 g methyldichlorosilane were introduced into a glass tube, and 11.5 mg of N-dimethylsilyl-N-methylacetamide were added with a microsyringe. 0.7 mg Of a toluene solution of a 0-valent platinum complex of divinylsiloxane (4.0 wt % platinum content) was added. The tube was sealed and then placed in a 50° C. oil bath where it was heated for 20 minutes. After cooling, the tube contents were analyzed by gas chromatography revealing an allyl chloride conversion of 92% and a chloropropylmethyldichlorosilane yield of 75%. The ratio between the chloropropylmethyldichlorosilane and propylmethyldichlorosilane was 4.57:1.

Example 17

Reaction between allyl chloride and methyldichlorosilane with platinum catalyst in the presence of a trimethylsilyl ester of methanesulfonic acid. 0.405 g Allyl chloride and 0.912 g methyldichlorosilane were introduced into a glass tube, and 15 mg of a trimethylsilyl ester of methanesulfonic acid were added with a microsyringe. 0.7 mg Of a toluene solution of a 0-valent platinum complex of divinylsiloxane (4.0 wt % platinum content) was added. The tube was sealed and placed in a 50° C. oil bath where it was heated for 20 hours. After cooling, the tube contents were analyzed by gas chromatography revealing an allyl chloride conversion of 97% and a chloropropylmethyldichlorosilane yield of 83%. The ratio between the chloropropylmethyldichlorosilane and propylmethyldichlorosilane was 5.69:1.

Comparative Example 8

Reaction between allyl chloride and methyldichlorosilane with platinum catalyst in the presence of methanesulfonic acid. 0.405 g Allyl chloride and 0.912 g methyldichlorosilane were introduced into a glass tube, and 8 mg of methanesulfonic acid were added with a microsyringe. 0.7 mg Of a toluene solution of a 0-valent platinum complex of divinylsiloxane (4.0 wt % platinum content) was added. The tube was sealed and placed in a 50° C. oil bath where it was heated for 20 hours. After cooling, the tube contents were analyzed by gas chromatography revealing an allyl chloride conversion of 98% and a chloropropylmethyldichlorosilane yield of 68%. The ratio between the chloropropylmethyldichlorosilane and propylmethyldichlorosilane was 2.26:1.

Example 18

Reaction between allyl chloride and methyldichlorosilane with platinum catalyst in the presence of bis(2-ethylhexyl) hydrogen phosphate. 0.327 g Allyl chloride and 0.751 g methyldichlorosilane were introduced into a glass tube, and 3.5 mg of bis(2-ethylhexyl) hydrogen phosphate were added with a microsyringe. 2.2 mg Of a toluene solution of a 0-valent platinum complex of divinylsiloxane (0.4 wt % platinum content) were added. The tube was sealed and placed in a 80° C. oil bath where it was heated for 15 minutes. After cooling, the tube contents were analyzed by gas chromatography revealing an allyl chloride conversion of 97% and a chloropropylmethyldichlorosilane yield of 83%. The ratio between the chloropropylmethyldichlorosilane and propylmethyldichlorosilane was 6.35:1.

Example 19

Reaction between allyl chloride and methyldichlorosilane with platinum catalyst in the presence of N-hydroxysuccinimide. 0.361 g Allyl chloride and 0.829 g methyldichlorosilane were introduced into a glass tube, and a 40 wt % ethanol solution of 10 mg of N-hydroxysuccinimide was added with a microsyringe. 2.3 mg Of a toluene solution of a 0-valent platinum complex of divinylsiloxane (0.4 wt % platinum content) were added. The tube was sealed and placed into a 80° C. oil bath where it was heated for 72 hours. After cooling, the tube contents were analyzed by gas chromatography, revealing an allyl chloride conversion of 95% and a chloropropylmethyldichlorosilane yield of 73%. The ratio between the chloropropylmethyldichlorosilane and propylmethyldichlorosilane was 3.07:1.

Example 20

Reaction between allyl chloride and methyldichlorosilane with platinum catalyst in the presence of trimethyl phosphate. 0.370 g Allyl chloride and 0.841 g methyldichlorosilane were introduced into a glass tube, and 7 mg of trimethyl phosphate were added with a microsyringe. 2.5 mg Of a toluene solution of a 0-valent platinum complex of divinylsiloxane (0.4 wt % platinum content) were added. The tube was sealed and placed in a 80° C. oil bath where it was heated for 1 hour. After cooling, the tube contents were analyzed by gas chromatography revealing an allyl chloride conversion of 64% and a chloropropylmethyldichlorosilane yield of 65%. The ratio between the chloropropylmethyldichlorosilane and propylmethyldichlorosilane was 6.44:1.

Example 21

Reaction between allyl chloride and methyldichlorosilane with platinum catalyst in the presence of triethyl phosphate. 0.370 g Allyl chloride and 0.841 g methyldichlorosilane were introduced into a glass tube, and 8.5 mg of triethyl phosphate were added with a microsyringe. 2.5 mg Of a toluene solution of a 0-valent platinum complex of divinylsiloxane (0.4 wt % platinum content) were added. The tube was sealed and placed in a 80° C. oil bath where it was heated for 1 hour. After cooling, the tube contents were analyzed by gas chromatography revealing an allyl chloride conversion of 84% and a chloropropylmethyldichlorosilane yield of 75%. The ratio between the chloropropylmethyldichlorosilane and propylmethyldichlorosilane was 7.02:1.

Example 22

Reaction between allyl chloride and methyldichlorosilane with platinum catalyst in the presence of 8-hydroxyquinoline. 0.376 g Allyl chloride and 0.850 g methyldichlorosilane were introduced into a glass tube, and 8 mg of 8-hydroxyquinoline were added with a microsyringe. 2.5 mg Of a toluene solution of a 0-valent platinum complex of divinylsiloxane (0.4 wt % platinum content) were added. The tube was sealed and placed in a 80° C. oil bath where it was heated for 1 hour. After cooling, the tube contents were analyzed by gas chromatography revealing an allyl chloride conversion of 99% and a chloropropylmethyldichlorosilane yield of 79%. The ratio between the chloropropylmethyldichlorosilane and propylmethyldichlorosilane was 3.83:1.

Example 23

Reaction between allyl chloride and methyldichlorosilane with platinum catalyst in the presence of 3-trimethylsilyl-2-oxazolidinone. 0.368 g Allyl chloride and 0.831 g methyldichlorosilane were introduced into a glass tube, and 39 mg of 3-trimethylsilyl-2-oxazolidinone were added with a microsyringe. 2.5 mg Of a toluene solution of a 0-valent platinum complex of divinylsiloxane (0.4 wt % platinum content) were added. The tube was sealed and placed in a 80° C. oil bath where it was heated for 1 hour. After cooling, the tube contents were analyzed by gas chromatography revealing an allyl chloride conversion of 88% and a chloropropylmethyldichlorosilane yield of 72%. The ratio between the chloropropylmethyldichlorosilane and propylmethyldichlorosilane was 5.04:1.

Example 24

Reaction between allyl chloride and methyldichlorosilane with platinum catalyst in the presence of 2-hydroxypyridine. 0.361 g Allyl chloride and 0.831 g methyldichlorosilane were introduced into a glass tube, and a 1 wt % toluene solution of 80 mg of 2-hydroxypyridine was added with a microsyringe. 2.5 mg of a toluene solution of a 0-valent platinum complex of divinylsiloxane (0.4 wt % platinum content) were added. The tube was sealed and placed in a 80° C. oil bath where it was heated for 72 hours. After cooling, the tube contents were analyzed by gas chromatography revealing an allyl chloride conversion of 99% and a chloropropylmethyldichlorosilane yield of 79%. The ratio between the chloropropylmethyldichlorosilane and propylmethyldichlorosilane was 4.0:1.

Example 25

Reaction between styrene and methyldichlorosilane with platinum catalyst in the presence of sodium 1-octanesulfonate. 624 mg Styrene and 732 mg methyldichlorosilane were introduced into a glass tube, and 40 mg of sodium 1-octanesulfonate were added. 0.9 mg Of a toluene solution of a 0-valent platinum complex of divinylsiloxane (0.4 wt % platinum content) was added. The tube was sealed and placed in a 100° C. oil bath where it was heated for 20 hours. After cooling, the tube contents were analyzed by gas chromatography revealing a styrene conversion of 71% and a phenethylmethyldichlorosilane yield of 46%. The ratio between the phenethylmethyldichlorosilane and the (α-methylbenzyl)methyldichlorosilane was 18:1.

Example 26

Reaction between styrene and methyldichlorosilane with platinum catalyst in the presence of sodium cyclohexylsulfamate. 427 mg Styrene and 498 mg methyldichlorosilane were introduced into a glass tube, and 38 mg of sodium cyclohexylsulfamate were added. 1 mg Of a toluene solution of a 0-valent platinum complex of divinylsiloxane (0.4 wt % platinum content) was added. The tube was sealed and placed in a 50° C. oil bath where it was heated for 72 hours. After cooling, the tube contents were analyzed by gas chromatography revealing a styrene conversion of 85% and a phenethylmethyldichlorosilane yield of 70%. The ratio between the phenethylmethyldichlorosilane and the (α-methylbenzyl)methyldichlorosilane was 8.7:1.

Example 27

Reaction between styrene and methyldichlorosilane with platinum catalyst in the presence of sodium dodecylsulfate. 427 mg Styrene and 498 mg methyldichlorosilane were introduced into a glass tube, and 55 mg of sodium dodecylsulfate was added. 1 mg Of a toluene solution of a 0-valent platinum complex of divinylsiloxane (0.4 wt % platinum content) was added. The tube was sealed and placed in a 100° C. oil bath where it was heated for 20 hours. After cooling, the tube contents were analyzed by gas chromatography revealing a styrene conversion of 45% and a phenethylmethyldichlorosilane yield of 20%. The ratio between the phenethylmethyldichlorosilane and the (α-methylbenzyl)methyldichlorosilane was 34:1.

Comparative Example 9

Reaction between allyl chloride and methyldichlorosilane with platinum catalyst (no substance acting as auxiliary catalyst). 0.405 g Allyl chloride and 0.912 g methyldichlorosilane were introduced into a glass tube, and 0.7 mg Of a toluene solution of a 0-valent platinum complex of divinylsiloxane (4.0 wt % platinum content) was added. The tube was sealed and placed in a 50° C. oil bath where it was heated for 20 hours. After cooling, the tube contents were analyzed by gas chromatography, revealing an allyl chloride conversion of 99% and a chloropropylmethyldichlorosilane yield of 62%. The ratio between the chloropropylmethyldichlorosilane and propylmethyldichlorosilane was 1.66:1.

Comparative Example 10

Reaction between allyl chloride and methyldichlorosilane with platinum catalyst (no substance acting as auxiliary catalyst). 0.327 g Allyl chloride and 0.751 g methyldichlorosilane were introduced into a glass tube, and 2.2 mg of a toluene solution of a 0-valent platinum complex of divinylsiloxane (0.4 wt % platinum content) were added. The tube was sealed and placed in a 80° C. oil bath where it was heated for 15 minutes. After cooling, the tube contents were analyzed by gas chromatography revealing an allyl chloride conversion of 99% and a chloropropylmethyldichlorosilane yield of 72%. The ratio between the chloropropylmethyldichlorosilane and propylmethyldichlorosilane was 2.69:1.

Example 28

Reaction between allyl chloride and trichlorosilane with platinum catalyst in the presence of tris(butoxyethyl) phosphate. 0.367 g Allyl chloride and 0.976 g trichlorosilane were introduced into a glass tube, and 2 mg of tris(butoxyethyl) phosphate were added with a microsyringe. 5 mg Of a toluene solution of a 0-valent platinum complex of divinylsiloxane (0.2 wt % platinum content) were added. The tube was sealed and placed in a 100° C. oil bath where it was heated for 1 hour. After cooling, the tube contents were analyzed by gas chromatography revealing an allyl chloride conversion of 66% and a chloropropyltrichlorosilane yield of 79%. The ratio between the chloropropyltrichlorosilane and propyltrichlorosilane was 7.47:1.

Example 29

Reaction between allyl chloride and trichlorosilane with platinum catalyst in the presence of bis(2-ethylhexyl) hydrogenphosphate. 0.327 g Allyl chloride and 0.870 g trichlorosilane were introduced into a glass tube, and 0.7 mg of bis(2-ethylhexyl) hydrogenphosphate was added with a microsyringe. 4.5 mg Of a toluene solution of a 0-valent platinum complex of divinylsiloxane (0.2 wt % platinum content) were added. The tube was sealed and placed in a 100° C. oil bath where it was heated for 1 hour. After cooling, the tube contents were analyzed by gas chromatography revealing an allyl chloride conversion of 72% and a chloropropyltrichlorosilane yield of 46%. The ratio between the chloropropyltrichlorosilane and propyltrichlorosilane was 6.65:1.

Example 30

Reaction between allyl chloride and trichlorosilane with platinum catalyst in the presence of tris(4-t-butylphenyl) phosphate. 0.327 g Allyl chloride and 0.873 g trichlorosilane were introduced into a glass tube, and 28 wt % toluene solution of 35 mg of tris(4-t-butylphenyl) phosphate was added with a microsyringe. 4.5 mg Of a toluene solution of a 0-valent platinum complex of divinylsiloxane (0.2 wt % platinum content) were added. The tube was sealed and placed in a 100° C. oil bath where it was heated for 1 hour. After cooling, the tube contents were analyzed by gas chromatography revealing an allyl chloride conversion of 99% and a chloropropyltrichlorosilane yield of 75%. The ratio between the chloropropyltrichlorosilane and propyltrichlorosilane was 3.20:1.

Example 31

Reaction between allyl chloride and trichlorosilane with platinum catalyst in the presence of dimethylsilyl acetamide (HMe$_2$SiNMeCOMe). 0.504 g Allyl chloride and 1.148 g trichlorosilane were introduced into a glass tube, and 4.5 mg of dimethylsilyl acetamide (HMe$_2$SiNMeCOMe) were added with a microsyringe. 7 mg Of a toluene solution of a 0-valent platinum complex of divinylsiloxane (0.2 wt % platinum content) were added. The tube was sealed and placed in a 100° C. oil bath where it was heated for 72 hours. After cooling, the tube contents were analyzed by gas chromatography revealing an allyl chloride conversion of 99% and a chloropropyltrichlorosilane yield of 74%. The ratio between the chloropropyltrichlorosilane and propyltrichlorosilane was 3.10:1.

Comparative Example 11

Reaction between allyl chloride and trichlorosilane with platinum catalyst (no substance acting as auxiliary catalyst). 0.327 g Allyl chloride and 0.873 g trichlorosilane were introduced into a glass tube, and 4.5 mg of a toluene solution of a 0-valent platinum complex of divinylsiloxane (0.2 wt % platinum content) were added. The tube was sealed and placed in a 100° C. oil bath where it was heated for 1 hour. After cooling, the tube contents were analyzed by gas chromatography revealing an allyl chloride conversion of 96% and a chloropropyltrichlorosilane yield of 42%. The ratio between the chloropropyltrichlorosilane and propyltrichlorosilane was 1.62:1.

What is claimed is:

1. A method of preparing an organosilicon compound comprising effecting a hydrosilylation reaction between (a) unsaturated compounds with terminal unsaturated groups and (b) silane compounds described by formula $HSiR^0{}_mW_{3-m}$, where W is selected from the group consisting of $C_1$ to $C_6$ alkoxy groups, $C_6$ to $C_{10}$ aryloxy groups, and halogen atoms, $R^0$ is an organic group, and m is 0, 1, or 2 in the presence of (c) a platinum catalyst and (d) an auxiliary catalyst selected from the group consisting of (1) silyl esters of acids derived from oxo acids of sulfur; (2) amide compounds having N—Si bonds; (3) urea compounds; (4) silyl esters of carbamic acid; (5) phosphoric acid compounds; and (6) cyclic compounds described by the following formulas selected from the group consisting of (i) hydroxypyridine compounds, (ii) 8-hydroxyquinoline compounds, (iii) oxazolidinone compounds, and (iv) N-hydroxysuccinimide compounds:

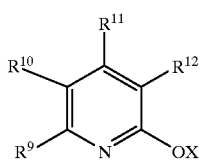

(i)

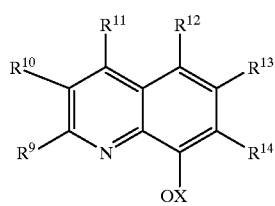

(ii)

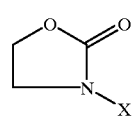

(iii)

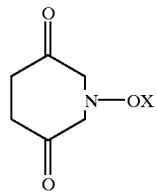

(iv)

where $R^9$, $R^{10}$, $R^{11}$, $R^{12}$, $R^{13}$, and $R^{14}$ are each independently selected from the group consisting of hydrogen atoms, halogen atoms, $C_1$ to $C_{10}$ alkyl groups, $C_6$ to $C_{10}$ aryl groups, $C_1$ to $C_{10}$ alkoxy groups, and groups described by $R^2{}_3Si$—, where each $R^2$ is independently selected from the group consisting of $C_1$ to $C_{10}$ hydrocarbon groups, $C_1$ to $C_{10}$ alkoxy groups, chlorine atoms, and hydrogen atoms with a maximum of 2 hydrogen atoms present; and X is a hydrogen atom or a group described by $R^2{}_3Si$—, where $R^2$ is the same as described above.

2. A method of preparing organosilicon compounds according to claim 1, where (d)(1) through (d)(5) of the auxiliary compounds are described by general formulas (d)(1): $R^1S(=O)_2OSiR^{21}{}_3$, where $R^1$ is selected from the group consisting of $C_1$ to $C_{10}$ alkyl groups, $C_6$ to $C_{18}$ aryl groups, groups described by $R^{18}{}_2N$—, where each $R^{18}$ is independently selected from the group consisting of $C_1$ to $C_{10}$ alkyl groups, $C_6$ to $C_{18}$ aryl groups, hydrogen atom with a maximum of 1 hydrogen atom present, $C_1$ to $C_{10}$ haloalkyl groups, $C_6$ to $C_{18}$ haloaryl groups, halogen atoms, $C_1$ to $C_{10}$ alkoxy groups, and siloxy groups described by formula $R^{30}{}_3SiO$—, where each $R^{30}$ is an independently selected $C_1$ to $C_6$ alkyl groups; and each $R^{21}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^1S(=O)_2O$—, where $R^1$ is the same as described above;

(d)(2): $R^3C(=O)NR^4SiR^{22}{}_3$, where $R^3$ is selected from the group consisting of $C_1$ to $C_{10}$ alkyl groups, $C_6$ to $C_{18}$ aryl groups, $C_1$ to $C_{10}$ haloalkyl groups, and $C_6$ to $C_{18}$ haloaryl groups; $R^4$ is a $C_1$ to $C_{10}$ hydrocarbon group or hydrogen atom; and each $R^{22}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^3C(=O)NR^4$—, where $R^3$ and $R^4$ are the same as above;

(d)(3): $R^5R^6NC(=O)NR^4X^1$, where $R^5$ and $R^6$ are each independently selected from the group consisting of hydrogen atoms, $C_1$ to $C_{10}$ alkyl groups, $C_6$ to $C_{18}$ aryl groups, $C_1$ to $C_{10}$ haloalkyl groups, $C_6$ to $C_{18}$ haloaryl groups, and silyl groups described by $R_3Si$—, where each R is an independently selected $C_1$ to $C_3$ alkyl group or hydrogen atom with a maximum of 2 hydrogen atoms present, $R^4$ is the same as described above; $X^1$ is selected from the group consisting of $R^{23}{}_3Si$— and hydrogen atoms, where each $R^{23}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^5R^6NC(=O)$—, where $R^5$ and $R^6$ are the same as described above;

(d)(4): $R^7R^8NC(=O)OSiR^{24}{}_3$, where $R^7$ and $R^8$ are each independently selected from the group consisting of $C_1$ to $C_{10}$ alkyl groups, $C_6$ to $C_{18}$ aryl groups, and hydrogen atoms with a maximum of 1 hydrogen atom present; and each $R^{24}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $R^7R^8NC(=O)$—, where $R^7$ and $R^8$ are the same as described above; and (d)(5): $(R^{16}O)_3P(=O)$, where each $R^{16}$ is independently selected from the group consisting of hydrogen atoms with a maximum of 2 hydrogen atoms present, $C_1$ to $C_{10}$ alkyl groups, $C_6$ to $C_{18}$ aryl groups, $C_1$ to $C_{10}$ haloalkyl groups, $C_6$ to $C_{18}$ haloaryl groups, and a maximum of 2 silyl groups represented by $R^{25}{}_3Si$—, where each $R^{25}$ is independently selected from the group consisting of $C_1$ to $C_{10}$ hydrocarbon groups, $C_1$ to $C_{10}$ alkoxy groups, chlorine atoms, hydrogen atoms with a maximum of 2 hydrogen atoms present, and $(R^{15}O)_2P(=O)O$—, where each $R^{15}$ is independently selected from the group consisting of hydrogen atoms with a maximum of 2 hydrogen atoms present, $C_1$ to $C_{10}$ alkyl groups, $C_6$ to $C_{18}$ aryl groups, $C_1$ to $C_{10}$ haloalkyl groups, and $C_6$ to $C_{18}$ haloaryl groups.

3. A method of preparing organosilicon compounds according to claim 1, where component (d) is an in situ formed auxiliary catalyst.

4. A method of preparing organosilicon compounds according to claim 1, where component (a) is selected from the group consisting of styrene or styrene derivative and allyl compounds.

5. A method of preparing organosilicon compounds according to claim 1, where component (b) is selected from the group consisting of trimethoxysilane, methyldimethoxysilane, dimethylmethoxysilane, triethoxysilane, methyldiethoxysilane, dimethylethoxysilane, dimethylchlorosilane, methyldichlorosilane, and trichlorosilane.

6. A method of preparing organosilicon compounds according to claim 1, where (d)(1) is selected from the group consisting of silyl esters of alkylsulfonic acids and silyl esters of arylsulfonic acids.

7. A method of preparing organosilicon compounds according to claim 1, where (d)(2) is selected from the group consisting of N-dialkylsilylacetamides and N-dialkylsilyl-N-alkylacetamides.

8. A method of preparing organosilicon compounds according to claim 1, where (d)(3) is selected from the group consisting of urea and N,N'-bis(trialkylsilyl)ureas.

9. A method of preparing organosilicon compounds according to claim 1, where (d)(4) is a trialkylsilyl-N,N-dialkylcarbamate.

10. A method of preparing organosilicon compounds according to claim 1, where (d)(5) is a trialkyl phosphate.

11. A method of preparing organosilicon compounds according to claim 1, where (d)(6) is selected from the group consisting of 2-hydroxypyridine, 8-hydroxyquinoline, oxazolidinone, 3-trimethylsilyl-2-oxazolidinone, and N-hydroxysuccinimide.

12. A method of preparing organosilicon compounds according to claim 1, where component (d) comprises 0.01 to 20 Wt. %, relative to the total weight of components (a) and (b).

13. A method of preparing organosilicon compounds according to claim 1, where component (d) comprises 0.05 to 10 Wt. %, relative to the total weight of components (a) and (b).

14. A method of preparing organosilicon compounds according to claim 1, where component (d) is an in situ formed auxiliary catalyst formed from a metal salt compound.

* * * * *